(12) United States Patent
Kim et al.

(10) Patent No.: US 8,895,515 B2
(45) Date of Patent: Nov. 25, 2014

(54) COSMETIC COMPOSITION FOR SKIN CELL REGENERATION MIMICKING EXTRACELLULAR MATRIX

(75) Inventors: Mi Jin Kim, Yongin-si (KR); Jong Won Shim, Yongin-si (KR); Yong Jin Kim, Suwon-si (KR); Eun Jung An, Suwon-si (KR); Chan Woo Lee, Suwon-si (KR); Soo Jin Lee, Yongin-si (KR); Jin Woong Kim, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 133 days.

(21) Appl. No.: 12/955,301

(22) Filed: Nov. 29, 2010

(65) Prior Publication Data

US 2011/0130339 A1 Jun. 2, 2011

(30) Foreign Application Priority Data

Nov. 30, 2009 (KR) .................. 10-2009-0116444
Nov. 8, 2010 (KR) .................. 10-2010-0110217

(51) Int. Cl.
*A61K 38/00* (2006.01)
*C07K 5/08* (2006.01)
*A61K 8/64* (2006.01)
*A61K 8/19* (2006.01)
*A61K 8/27* (2006.01)
*A61K 8/67* (2006.01)
*A61K 8/73* (2006.01)
*A61Q 19/08* (2006.01)

(52) U.S. Cl.
CPC ... *A61K 8/64* (2013.01); *A61K 8/19* (2013.01); *A61K 8/27* (2013.01); *A61K 8/67* (2013.01); *A61K 8/735* (2013.01); *A61Q 19/08* (2013.01); *A61K 2800/592* (2013.01)
USPC .................. 514/21.9; 514/18.6; 530/331

(58) Field of Classification Search
None
See application file for complete search history.

(56) References Cited

U.S. PATENT DOCUMENTS

| 8,022,038 B2 * | 9/2011 | Miyata et al. ............ 514/17.2 |
| 2003/0068297 A1 * | 4/2003 | Jain ........................... 424/85.1 |
| 2007/0207180 A1 | 9/2007 | Tanihara et al. |
| 2008/0057091 A1 * | 3/2008 | Abdellaoui et al. ......... 424/401 |

FOREIGN PATENT DOCUMENTS

| JP | 03137807 | * | 5/2003 |
| JP | 2003137807 A | * | 5/2003 |
| WO | WO 2007037060 A1 * | 4/2007 |

OTHER PUBLICATIONS

Farwick et. al. (Low Molecular Weight Hyaluronic Acid: Its effects on Epidermal Gene Expression and Skin Ageing, International Journal for Applied Science, SOWFW-Journal, vol. 134, p. 1-5 Nov. 2008.*
Office Action in related Chinese Application No. 201010575568.8; Date of Issue Mar. 4, 2013; 16 pages; In Chinese with English Translation.

* cited by examiner

*Primary Examiner* — Thomas S Heard
*Assistant Examiner* — Jeanette Lieb
(74) *Attorney, Agent, or Firm* — Nixon & Vanderhye PC

(57) ABSTRACT

The present invention relates to a cosmetic composition which mimics the extracellular matrix to stimulate the regeneration of skin cells, and more particularly to a cosmetic composition which contains active ingredients consisting of low-molecular-weight materials, which easily permeate through the skin, at a composition ratio similar to that in the extracellular matrix. The cosmetic composition stimulates the repair of the skin to maintain homeostasis and is effective for the regeneration of skin cells.

12 Claims, 3 Drawing Sheets

COSMETIC COMPOSITION FOR SKIN CELL REGENERATION MIMICKING EXTRACELLULAR MATRIX

This application claims priority to Korean Application No(s). 10-2009-0116444, filed 30 November 2009 and 10-2010-0110217, filed November 2010, the entire contents of each of which are hereby incorporated by reference.

TECHNICAL FIELD

The present invention relates to a cosmetic composition which mimics the extracellular matrix to stimulate the regeneration of skin cells, and more particularly to a cosmetic composition which contains active ingredients consisting of low-molecular-weight materials, which easily permeate through the skin, at a ratio similar to that of the extracellular matrix. The cosmetic composition of the present invention stimulates the repair of the skin to maintain homeostasis and is effective for the regeneration of skin cells.

BACKGROUND ART

All living organisms are aged as they grow older. Also, the skin undergoes an aging process. Efforts to delay this aging process have been continuously made, and thus the nature and causes of aging have been continuously studied. Skin aging can be broadly divided into two types: intrinsic aging and extrinsic aging. Intrinsic aging is the progressive deterioration in physical structure and biological function that occurs with advancing age. Extrinsic aging is caused by external factors such as sunlight. Both intrinsic aging and extrinsic aging result in structural changes in the skin, and consequently, the skin becomes dry, losses elasticity and develops wrinkles.

More specifically, the structural changes of the skin resulting from aging, the epidermal, dermal and subcutaneous tissues of the skin become thin. Also, the components of the extracellular matrix (ECM) that is attributable for the firmness and tightness of the skin change. The extracellular matrix is a three-dimensional structure which contains inorganic salts, nutrients, aqueous solutions such as waste materials, and large polysaccharide molecules. It forms a network in the space surrounding cells to maintain the shape of tissue and plays an important role in signaling between cells and regulating the growth and differentiation of cells.

ECM components that have been mimicked till now are mostly of animal origin. However, components of animal origin are generally used in cosmetic products, because they pose safety problems, such as infection with pathogens.

Collagen accounting for 70-80% of the extracellular matrix is a long fiber-like protein that increases the strength and elasticity of the skin. It is known to have a close connection with skin aging, that is, a reduction in elasticity or the formation of wrinkles. However, collagens which are currently used are mostly of animal origin and are polymers having a molecular weight of about 300,000 Da, and thus the absorption of these collagens themselves into the skin is limited.

Hyaluronic acid, an ECM component, serves to combine skin dermal cells with each other and to delivery nutrients and allows the skin to retain a suitable amount of water. However, because hyaluronic acid is a polymer which has a molecular weight ranging from several hundred thousands to several millions and is highly viscous, the application thereof in cosmetic products is limited and it is difficult to permeate through the skin when it is applied directly to the skin.

DISCLOSURE

Technical Problem

The present inventors have prepared a composition containing a tripeptide, a low-molecular-weight hyaluronic acid, a mineral component and vitamin, which are not of animal origin, but are of plant origin or prepared synthetically, and have found that, when the components of the composition are made to have a composition ratio similar to that of the extracellular matrix and they have low molecular weight such that they can permeate through the skin, they can stimulate the regeneration of skin cells, thereby completing the present invention.

It is, therefore, an object of the present invention to provide a cosmetic composition which mimics the extracellular matrix to stimulate the regeneration of skin cells and to repair damage to the skin.

Technical Solution

To achieve the above object, the present invention provides a cosmetic composition containing, as active ingredients, a tripeptide of glycine-proline-hydroxyproline (Gly-Pro-Hyp), a low-molecular-weight hyaluronic acid, a mineral component, and vitamin.

Advantageous Effects

According to the inventive cosmetic composition mimicking the extracellular matrix, a tripeptide, a low-molecular-weight hyaluronic acid, a mineral component and vitamin, can form a network in the space surrounding cells to maintain the shape of tissue and can regulate signaling between cells and the growth and differentiation of cells, thereby inhibiting skin aging, that is, a reduction in elasticity or the formation of wrinkles. Also, the low-molecular-weight molecules can be easily permeated through the skin, thereby stimulating the regeneration of skin cells and repairing damage to the skin.

MODE FOR INVENTION

Figure 1:
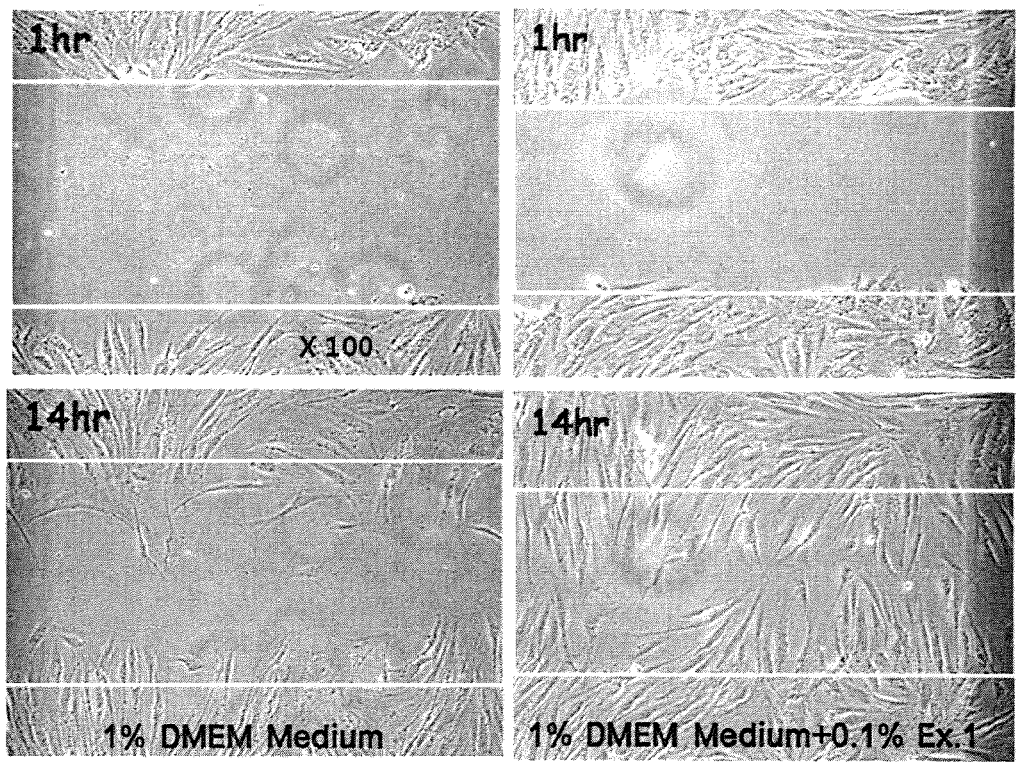
FIG. 1 is a micrograph showing the results of observing the wound repair ability of a composition according to the present invention.

The present invention provides a cosmetic composition containing, as active ingredients, a tripeptide of glycine-proline-hydroxyproline (Gly-Pro-Hyp), a low-molecular-weight hyaluronic acid, a mineral component, and vitamin.

Hereinafter, the present invention will be described in further detail.

The tripeptide that is used as an active ingredient in the present invention consists of the three amino acids, glycineproline-hydroxyproline (Gly-Pro-Hyp), stimulates the production of collagen, and has a high permeability through the skin, because it has low molecular weight. Also, the tripeptide is highly pure, because it is synthetically prepared. In addition, because it is not of animal origin, it does not pose safety concerns, such as infection with pathogens.

Where collagen is hydrolyzed by acid, various fragments are produced, and thus it is difficult to obtain tripeptide from collagen. Where collagen is hydrolyzed by enzyme, it is difficult to obtain a tripeptide having low molecular weight. For these reasons, according to the present invention, a uniform tripeptide can be obtained by retro-synthesis based on amino acids. The tripeptide that is used in the present invention can be prepared using any conventional method known in the art, and the synthesis method is not specifically limited.

The tripeptide in the present invention is contained in an amount of 0.001-3 wt % based on the total weight of the composition. If the content of the tripeptide is less than 0.001 wt %, the effect thereof will be insignificant, and if it is more than 3 wt %, a further increase in the effect thereof will not be obtained, and the production cost of the composition will be increased.

The low-molecular-weight hyaluronic acid that is used as an active ingredient in the present invention is easily absorbed into the skin and exhibits excellent skin-moisturizing, wrinkle-reducing, wound healing, and anti-inflammatory effects, compared to polymeric hyaluronic acid. The low-molecular-weight hyaluronic acid that is used in the present invention has a molecular weight of 500-10,000 Da. A hyaluronic acid having a molecular weight of less than 500 Da will be difficult to prepare and separate, and a hyaluronic acid having a molecular weight of more than 10,000 Da will be difficult to permeate through the skin such that the effect thereof will not be exhibited, and it will have increased viscosity, leading to poor formulation stability.

The low-molecular-weight hyaluronic acid that is used in the present invention can be prepared using any conventional method known in the art, and the preparation method is not specifically limited. For example, the low-molecular-weight hyaluronic acid can be prepared by reducing the molecular weight of polymeric hyaluronic acid using high-temperature heating and ultrasonic waves, an acidic or basic catalyst, a degradation catalyst such as ammonium peroxide, or hyaluronidase enzyme.

The low-molecular-weight hyaluronic acid that is used in the present invention may be used in an amount of 0.001-50 wt %, and preferably 0.01-10 wt %, based on the total weight of the composition.

The mineral component that is used in the present invention may be one or more selected from the group consisting of magnesium chloride, calcium chloride, potassium chloride, magnesium fluoride, manganese fluoride, manganese sulfate, zinc sulfate, magnesium sulfate and copper sulfate.

Magnesium chloride, calcium chloride and calcium chloride are known to participate in epidermal differentiation (J Clin Invest. 1992 February; 89(2): 530-538.), and mineral components such as magnesium fluoride, manganese fluoride, manganese sulfate, zinc sulfate, magnesium sulfate and copper sulfate are known to be required for cell homeostasis and skin protection.

The mineral component that is used in the present invention is contained in an amount of 0.001-3 wt % based on the total weight of the composition. If the content of the mineral component is less than 0.001 wt %, the effect thereof will be insignificant, and if it is more than 3 wt %, it can impair skin homeostasis.

Vitamin which is used as an active ingredient in the present invention is a component required for cell metabolism, improves the skin's barrier function and plays an important role in collagen synthesis. Vitamin that can be used in the present invention may be one or more selected from the group consisting of inositol, ascorbic acid, pantothenic acid, niacin, folic acid, thiamine, riboflavin, and derivatives thereof.

Vitamin which is used in the present invention is contained in an amount of 0.001-3 wt % based on the total weight of the composition. If the content of vitamin is less than 0.001 wt %, the effect thereof will be insignificant, and if it is more than 3 wt*, it can cause discoloration and bad smell, thus deteriorating the stability of the composition.

Hereinafter, the present invention will be described in further detail with reference to examples, but the scope of the present invention is not limited to these examples.

Example 1

According to the components and contents shown in Table 1 below, a composition mimicking the extracellular matrix was prepared. Herein, inositol and ascorbic acid were used as vitamins B and C, respectively, and niacinamide was used as a derivative of niacin (vitamin B3). Also, zinc sulfate, potassium chloride, calcium chloride, magnesium sulfate and copper sulfate were used as mineral components. Oligo hyaluronic acid was purchased from Bioland Ltd., Korea, and tripeptide was purchased from A & PEP Inc., Korea.

TABLE 1

| Components | Contents (wt %) |
| --- | --- |
| Oligo hyaluronic acid (weight-average molecular weight: 5,000 Da) | 0.6 |
| Tripeptide | 0.3 |
| Polylysine | 0.045 |
| Glutamine | 0.037 |
| Arginine | 0.015 |
| Isoleucine | 0.01 |
| Oleic acid | 0.002 |
| Linoleic acid | 0.002 |
| Alanine | 0.005 |
| Inositol | 0.002 |
| Niacinamide | 0.0002 |
| Ascorbic acid | 0.005 |
| Zinc sulfate | 0.043 |
| Potassium chloride | 0.03 |
| Calcium chloride | 0.012 |
| Magnesium sulfate | 0.01 |
| Copper sulfate | 0.0002 |
| Purified water | Balance |

Test Example 1

Cell Wound Repair Test

Figure 2:
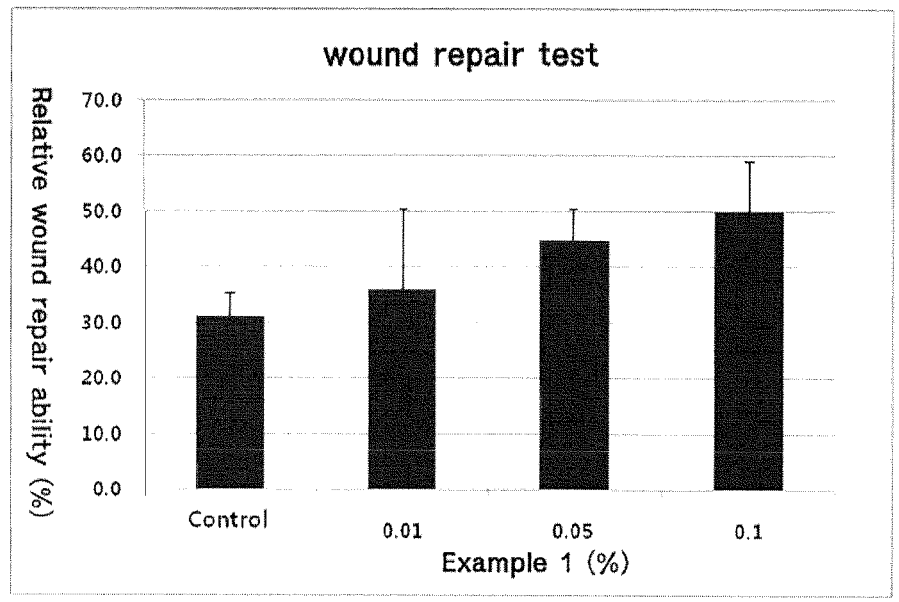
FIG. 2 is a graphic diagram showing the results of quantitatively analyzing the wound repair ability of a composition of the present invention at various concentrations.

Fibroblast cells isolated from human skin were seeded into 12-well plates at a density of $10^5$ cells per well and cultured to a confluence of about 90% in 1% FBS-containing DMEM medium (Dubelcco's Modified Eagle Medium; BRL, USA). A given area of the bottom of the plates was rubbed with a fine tip to remove cells, and a medium containing the composition of Example 1 was added to the plate. After 14 hours, the growth of the cells in the plate was observed with a microscope, and the results of the observation are shown in FIG. 1. Also, after 1 hour and 14 hours, the area having no cells (area of damaged cells) was measured using Image J program, and based on the results of the measurement, relative wound repair ability (%) was calculated according to the following equation 1, and the results of the calculation are shown in FIG. 2:

Relative wound repair ability (%)=damaged area at 1 hr−damaged area at 14 hr/damaged area at 1 hr×100 [Equation 1]

As can be seen in FIG. 1, the area of the damaged cells in the test group treated with the DMEM medium containing the composition of Example 1 was visibly reduced compared with the control treated with the DMEM medium alone. Also, as can be seen in FIG. 2, the relative wound repair ability of the test group was higher than that of the control group, and it was increased in a concentration-dependent manner.

This suggests that the inventive cosmetic composition mimicking the extracellular matrix can stimulate the regeneration of skin cells and can rapidly repair damage to the skin.

Test Example 2

Cell Proliferation Test

Fibroblast cells isolated from the skin of persons in their forties were seeded into 96-well plates at a density of $3\times10^3$ cells per well and cultured in M106 medium for 24 hours. As a control, 1% fetal bovine serum (FBS) was used, and as a positive control, 10% FBS was used. The cells were cultured in FBS medium containing 1% composition of Example 1 for 48 hours and 72 hours, and then subjected to an ELISA BrdU assay using a cell proliferation ELISA kit (Roche). The results of the assay are shown in FIG. 3.

Figure 3:
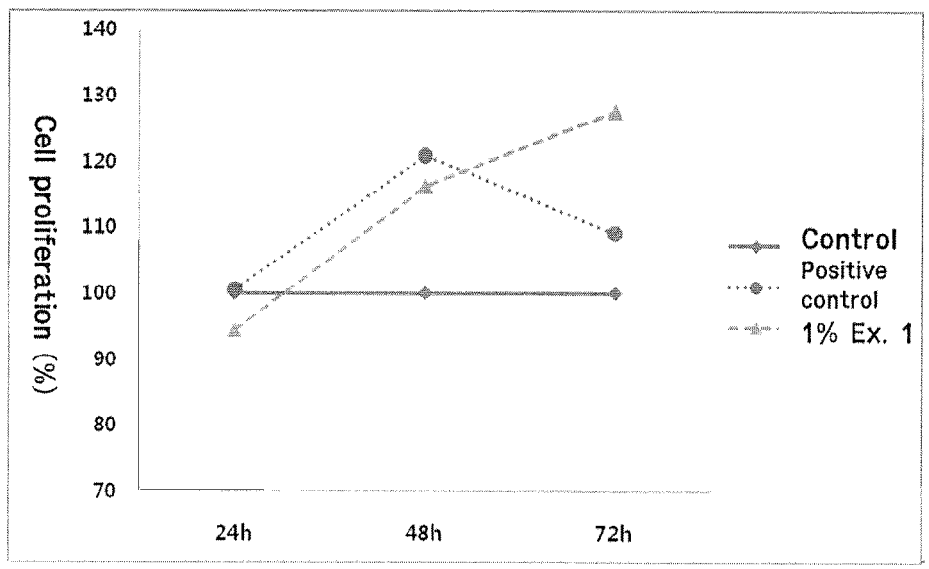
FIG. 3 is a graphic diagram showing the fibroblast proliferating effect of a composition according to the present invention.

As can be seen in FIG. 3, the composition of Example 1 showed a similar effect on cell proliferation compared to the positive control after 48 hours, and showed a significantly high cell proliferation effect compared to the positive control after 72 hours. This suggests that the inventive cosmetic composition mimicking the extracellular matrix has an excellent on the proliferation of skin fibroblast cells.

Test Example 3

Skin Safety Test

In order to examine whether the composition prepared in Example 1 causes allergic dermatitis and primary irritant contact dermatitis, a patch test was carried out on 40 healthy adults (average age: 39.6 years; having no skin lesion) using 20 μl of the composition of Example 1 in an IQ chamber. The patch was applied for 24 hours, and after removing the area to which the patch was applied, the area was marked. After 30 minutes and 24 hours, the marked area was observed, and whether the composition irritated the skin was evaluated according to the following standards (modifications of CTFA guideline (1981) and Frosch & Kligman (1979)) shown in Table 2 below.

TABLE 2

| Score | Characteristic |
| --- | --- |
| 0 | No reaction |
| 1 | Erythema, either spotty or diffuse |

TABLE 2-continued

| Score | Characteristic |
| --- | --- |
| 2 | Moderate uniform erythema |
| 3 | Intense erythema with eczema |
| 4 | Intense erythema with eczema and vesicles |

Grade I (no irritation): below 1

Grade II (slight irritation): below 3

Grade III (moderate irritation): below 5

Grade IV (intense irritation): above 5

The results of carrying out the patch test as described above indicated that the composition of the present invention showed an irritation score of zero, suggesting that the composition of the present invention is not irritative and is a very safe cosmetic composition.

Test Example 4

Test for Effect on Human Skin Elasticity

According to the components and contents shown in Table below, a cream formulation (Example 1) containing the composition of Example 1 and a cream formulation (Comparative Example 1) not containing the composition of Example 1 were prepared using a conventional method.

TABLE 3

| Components | Example 2 (wt %) | Comparative Example 1 (wt %) |
| --- | --- | --- |
| Glyceryl stearate | 1 | 1 |
| Pentaerythrityl tetraethyl hexanoate | 5 | 5 |
| Hydrogenated polydecene | 1 | 1 |
| Vegetable squalane | 2 | 2 |
| Behenyl alcohol | 6.5 | 6.5 |
| Cetearyl alcohol | 0.6 | 0.6 |
| PEG-60 glyceryl isostearate | 2.5 | 2.5 |
| Dimethicone | 2.5 | 2.5 |
| Glycerin | 6 | 6 |
| Butylene glycol | 5 | 5 |
| Mixture of active ingredients | 5 | 5 |
| Xanthan gum | 0.1 | 0.1 |
| Example 1 | 5 | — |
| Preservative | Trace | Trace |
| Pigment | Trace | Trace |
| Fragrance | Trace | Trace |
| Purified water | Balance | Balance |

Figure 4:
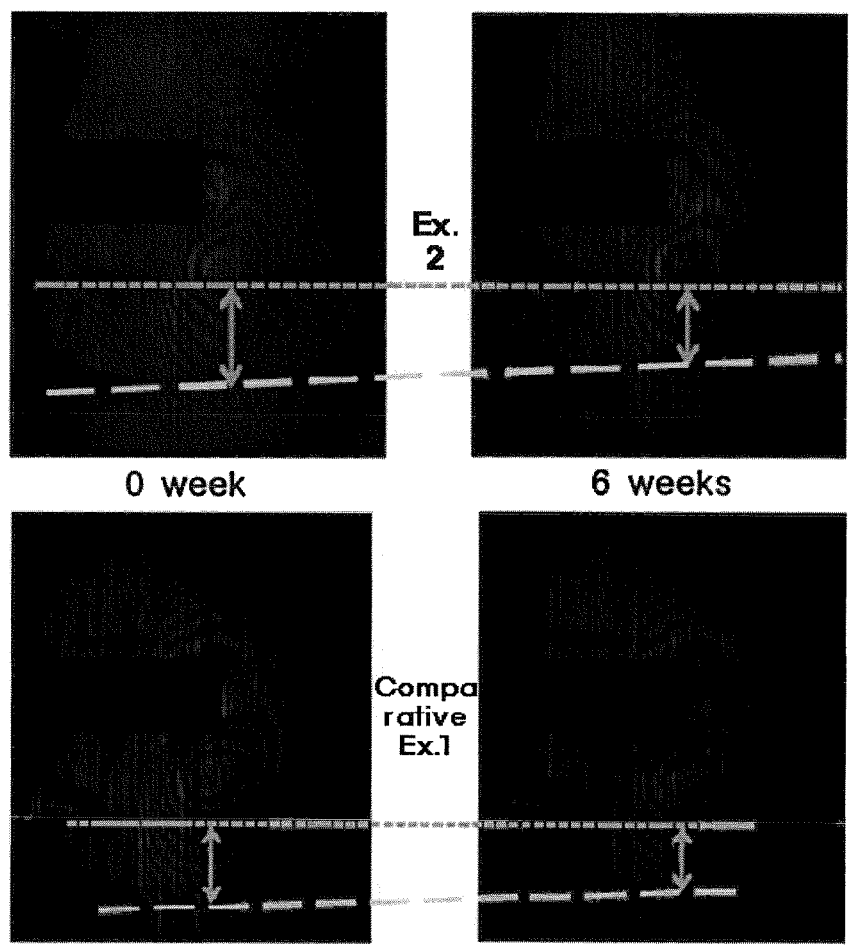
FIG. 4 is a Moire image showing the effect of the inventive composition on an improvement in skin elasticity.

To measure the effect of the cream of Example 2 on the improvement in the elasticity of facial skin, Twenty-two 35-45 years old women were divided into two groups. One group was applied with the cream of Example 2 twice (morning and evening) a day, and the other group was applied with applied with the cream of Comparative Example 1 twice (morning and evening) a day. After 3 weeks and 6 weeks, the droop angle of the face was measured using Moire images capable of measuring skin elasticity, thereby measuring the facial droop angle before and after the application of the cream. The Moire images are shown in FIG. 4, and the results of measuring the facial droop angle are shown in Table 4 below. The numerical values shown in Table 4 are the averages of the numerical values obtained for the subjects of each group.

TABLE 4

| Angle (°) | 0 week | 3 weeks | 6 weks |
| --- | --- | --- | --- |
| Example 2 | 35.42 | 34.93 | 33.59 |
| Comparative Example 1 | 36.21 | 35.97 | 35.52 |

As can be seen in FIG. 4 and Table 4, after 6 weeks of use, Comparative Example 1 and Example 2 showed decreases in facial droop angle of 1.91% and 5.17%, respectively. It could be seen that the composition of Example 2 was more effective in improving the facial droop angle, suggesting that the composition of the present invention has an effect of increasing skin elasticity.

Test Example 5

Test for Skin Tone Improvement

When the function of skin cells is recovered and the regeneration thereof is stimulated, non-uniform skin tone becomes uniform. In order to examine the effect of the inventive composition on the improvement of skin tone, twenty-two 35-45 years old women were divided into two groups. One group was applied with the cream of Example 2 twice (morning and evening) a day, and the other group was applied with applied with the cream of Comparative Example 1 twice (morning and evening) a day. After 3 weeks and 6 weeks, the degree of improvement in the skin tone of the subjects was evaluated using Facial Stage DM-3 (Moritex, Japan). The non-uniformity of skin tone was measured, and the results of the measurement are shown in Table 5 below.

TABLE 5

| Skin tone non-uniformity (%) | 0 week | 3 weeks | 6 weeks |
| --- | --- | --- | --- |
| Example 2 | 8.14 | 8.07 | 7.81 |
| Comparative Example 1 | 8.12 | 8.10 | 8.03 |

As can be seen from the results in Table 5 above, in the evaluation conducted after 6 weeks, the non-uniformity of skin tone was decreased by 4.05% for Example 2, whereas it was decreased by 1.11% for Comparative Example 1. This suggests that the composition of the present invention is effective in making skin tone uniform.

Formulation Example 1

Skin Lotion

According to the components and contents shown in Table 6 below, a skin lotion formulation containing the composition of Example 1 was prepared using a conventional method.

TABLE 6

| Components | Contents (wt %) |
| --- | --- |
| Betaine | 3.0 |
| Natto gum | 3.0 |
| Cellulose gum | 0.005 |
| Ethanol | 10.0 |
| Polyoxyethylene hydrogenated castor oil | 0.2 |
| Tocopherol acetate | 2.0 |

TABLE 6-continued

| Components | Contents (wt %) |
| --- | --- |
| Example 1 | 10 |
| Preservative | Trace |
| Pigment | Trace |
| Fragrance | Trace |
| Purified water | Balance |

Formulation Example 2

Milk Lotion Formulation

According to the components and contents shown in Table 7 below, a milk lotion formulation containing the composition of Example 1 was prepared using a conventional method.

TABLE 7

| Components | Contents (wt %) |
| --- | --- |
| Cetyl ethyl hexanoate | 4.0 |
| Cetostearyl alcohol | 1.0 |
| Lipophilic monostearate | 1.0 |
| Squalane | 0.5 |
| Example 1 | 5.0 |
| Polysorbate 60 | 1.5 |
| Sorbitan sesquioleate | 0.5 |
| Glycerin | 5.0 |
| Triethanolamine | 0.5 |
| Carboxyvinyl polymer | 0.2 |
| Preservative | Trace |
| Pigment | Trace |
| Fragrance | Trace |
| Purified water | Balance |

Formulation Example 3

Cream

According to the components and contents shown in Table 8 below, a cream formulation containing the composition of Example 1 was prepared using a conventional method.

TABLE 8

| Components | Contents (wt %) |
| --- | --- |
| Glyceryl stearate | 3.0 |
| Polysorbate 60 | 1.0 |
| Cetostearate | 2.5 |
| Beewax | 1.0 |
| Squalane | 2.0 |
| Sorbitan sesquioleate | 0.5 |
| Cetyl ethyl hexanoate | 0.5 |
| Liquid paraffin | 5.0 |
| Mixture of active ingredients | 5.0 |
| Glycerin | 3.0 |
| Propylene glycol | 3.0 |
| Example 1 | 5.0 |
| Preservative | Trace |
| Pigment | Trace |
| Fragrance | Trace |
| Purified water | Balance |

The invention claimed is:
1. A cosmetic composition containing, as active ingredients, a tripeptide, a low-molecular-weight hyaluronic acid, a mineral component and vitamin; wherein the low-molecular-weight hyaluronic acid has a molecular weight of 500-5,000 Da;

wherein the cosmetic composition contains only one tripeptide with a sequence of glycine-proline-hydroxyproline (Gly-Pro-Hyp).

2. The cosmetic composition of claim 1, wherein the tripeptide is contained in an amount of 0.001-3 wt % based on the total weight of the composition.

3. The cosmetic composition of claim 1, wherein the low-molecular-weight hyaluronic acid is contained in an amount of 0.001-50 wt % based on the total weight of the composition.

4. The cosmetic composition of claim 1, wherein the mineral component is one or more selected from the group consisting of magnesium chloride, calcium chloride, potassium chloride, magnesium fluoride, manganese fluoride, manganese sulfate, zinc sulfate, magnesium sulfate and copper sulfate.

5. The cosmetic composition of claim 1, wherein the mineral component is contained in an amount of 0.001-3 wt % based on the total weight of the composition.

6. The cosmetic composition of claim 1, wherein the vitamin is one or more selected from inositol, ascorbic acid, pantothenic acid, niacin, folic acid, thiamine, riboflavin, and derivatives thereof.

7. The cosmetic composition of claim 1, wherein the vitamin is contained in an amount of 0.001-3 wt % based on the total weight of the composition.

8. The cosmetic composition of claim 1, wherein the composition is used to stimulate the regeneration of skin cell.

9. The cosmetic composition of claim 1, wherein the composition is used to repair damage to skin.

10. The cosmetic composition of claim 1, wherein the composition is used to inhibit skin aging.

11. The cosmetic composition of claim 1, wherein the composition is used to increase skin elasticity.

12. The cosmetic composition of claim 1, wherein the composition is used to increase skin tone.

\* \* \* \* \*